US005874583A

United States Patent [19]

Shutske et al.

[11] Patent Number: 5,874,583
[45] Date of Patent: Feb. 23, 1999

[54] 2,3-DIHYDRO-1H-ISOINDOLE DERIVATIVES

[75] Inventors: Gregory Michael Shutske, Flemington; Kevin James Kapples, Little York, both of N.J.

[73] Assignee: Hoechst Marion Roussel Inc., Kansas City, Mo.

[21] Appl. No.: 935,280

[22] Filed: Sep. 22, 1997

Related U.S. Application Data

[60] Continuation of Ser. No. 477,841, Jun. 7, 1995, abandoned, which is a division of Ser. No. 288,844, Aug. 11, 1994, Pat. No. 5,567,718.

[51] Int. Cl.$^6$ .............................. C07D 401/04
[52] U.S. Cl. ........................................ 546/200
[58] Field of Search .......................... 546/200

[56] References Cited

U.S. PATENT DOCUMENTS

| | | | |
|---|---|---|---|
| 2,957,872 | 10/1960 | Huebner | 548/472 |
| 3,031,458 | 4/1962 | Huebner | 548/472 |
| 3,084,167 | 4/1963 | Rice et al. | 548/472 |
| 3,091,568 | 5/1963 | Bub et al. | 548/472 |
| 3,322,631 | 5/1967 | Sprague et al. | 548/472 |
| 3,849,570 | 11/1974 | Raschack et al. | 548/472 |
| 3,875,165 | 4/1975 | Archibald et al. | 546/161 |
| 3,947,451 | 3/1976 | Jonsson et al. | 546/18 |
| 4,000,287 | 12/1976 | Werner et al. | 514/323 |
| 4,038,407 | 7/1977 | Eberlein et al. | 514/373 |
| 4,053,615 | 10/1977 | Boyle et al. | 514/318 |
| 4,072,499 | 2/1978 | Bollinger et al. | 504/252 |
| 4,115,398 | 9/1978 | Nakamura | 548/454 |
| 4,124,375 | 11/1978 | Bollinger et al. | 504/286 |
| 4,289,781 | 9/1981 | Bengtsson et al. | 546/200 |
| 4,291,042 | 9/1981 | Ward | 546/114 |
| 4,309,541 | 1/1982 | Werner | 546/208 |
| 4,724,235 | 2/1988 | Shanklin et al. | 514/212 |
| 4,999,355 | 3/1991 | Comte et al. | 514/255 |
| 5,026,707 | 6/1991 | Nixon et al. | 514/255 |
| 5,053,413 | 10/1991 | Desai | 514/323 |
| 5,196,434 | 3/1993 | Taverne et al. | 514/278 |
| 5,283,263 | 2/1994 | Norden | 514/651 |
| 5,424,318 | 6/1995 | Sugomoto et al. | 514/325 |

FOREIGN PATENT DOCUMENTS

| | | |
|---|---|---|
| 0026749 | 4/1981 | European Pat. Off. . |
| 2082569 | 3/1982 | European Pat. Off. . |
| 0326106 | 8/1989 | European Pat. Off. . |
| 0643057 | 3/1995 | European Pat. Off. . |
| 0760368 | 3/1997 | European Pat. Off. . |
| 2374847 | 7/1978 | France . |
| 1425578 | 2/1976 | United Kingdom . |

OTHER PUBLICATIONS

Truitt, et al., New Compounds vol. 8, 731 (1965).
Suzuki, et al., J. Heterocyclic Chem. 16, p. 645 (1979).
Huffman, J. Heterocyclic Chem. 24, pp. 549–553 (1987).
Hussein, et al., Asian J. of Chemistry, vol. 3, No. 1, p. 30 (1991).
Bonnett, et al., J. Chem. Soc., Perkin Trans., 1432 (1973).
Kurita et al., Am. Chem. Soc., Div. Org. Coat. Plast. Chem. Pop., 33, p. 177 (1973).
CA 109:6377 Moorman et al., (1987).
CA 118:30378, Rodier et al., (1992).
CA 115:49312, Hussein et al., (1991).
CA 115:136387, Hansen et al., (1991).
Whitaker, et al., Annal. of the New York Academy of Science, vol. 600, 109–110 (1990).
Principles of Psychopharmacology, Clark et al., Academic Press, NY, 166–167 (1970).
CA 77:5526, Cotrel, et al., (1972).
Chemical Abstracts, vol. 56, No. 1, column 404–g, K. Nakajima (1962).
R.A. Glennon, et al., J. Med. Chem. vol. 32, No. 8, 1921–1926 (1989).
Kanevskaya, et al., Zh. Obschch Khim. vol. 29, pp. 1903–1906 (1957).
Mndzhoyan et al., Izv. Akad. Nauk. Arm.SSR KHIM, Nauki, vol. 15, pp. 95–100 (1962).
Chemical Abstracts, vol. 115, No. 5, abstract No. 49312k, Hussein, et al., (1991).
Zee–Cheng, et al., J. Med. Chem. vol. 28, No. 9, pp. 1216–1222, (1985).
Goto et al., CA CA 114:81261.
Okazaki et al., CA 109:170232 (1988).
Mohri et al., CA 119:95325 (1993).
Streicher et al., CA 93:204981 (1980).
The Condensed Chemical Dictionary 10th ed. by Hawley, p. 90 (1981).
R.A. Glennon, J. of Medicinal Chemistry, vol. 30, No. 1, pp. 1–12 (1987).
CA 84:12490, Carvajal et al., (1976).

*Primary Examiner*—Jane Fan
*Attorney, Agent, or Firm*—Frommer Lawrence & Haug LLP

[57] ABSTRACT

2,3-dihydro-1H-isoindole derivatives of the formula

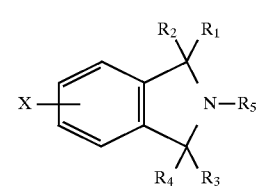

where $R_1$–$R_5$ and X are defined herein which are useful as serotonin reuptake inhibitors are disclosed. As such, these compounds may be useful for the treatment of depression, obsessive-compulsive disorders, stuttering and trichotillomania.

3 Claims, No Drawings

2,3-DIHYDRO-1H-ISOINDOLE DERIVATIVES

This is a continuation of application Ser. No. 08/477,841, filed Jun. 7, 1995, now AB which is a division of application Ser. No. 08/288,844, filed Aug. 11, 1994, now issued as U.S. Pat. No. 5,567,718, which are herein incorporated by reference.

The present invention relates to 2,3-dihydro-1H-isoindole derivatives of the formula

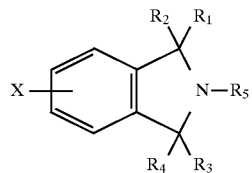

where
$R_1$ is hydrogen, loweralkyl, aryl, arylloweralkyl, —$(CH_2)_n$ $NR_6R_7$, $R_2$ is hydrogen or $OR_9$;
or $R_1$ and $R_2$ can be taken together to form a carbonyl group; or

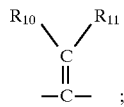

$R_3$ is hydrogen, and $R_4$ is hydrogen or $OR_9$;
or $R_3$ and $R_4$ can be taken together to form a carbonyl group;
$R_5$ is

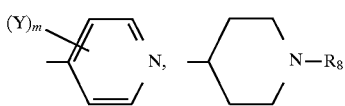

or —$(CH_2)_p NR_6R_7$;
$R_6$ is loweralkyl, arylloweralkyl;
$R_7$ is loweralkyl, arylloweralkyl;
$R_8$ is hydrogen, loweralkyl or arylloweralkyl;
$R_9$ is hydrogen, loweralkyl;
$R_{10}$ is hydrogen or loweralkyl;
$R_{11}$ is hydrogen or loweralkyl;
X is hydrogen, halogen, trifluoromethyl, hydroxy, loweralkoxy or cyano;
Y is hydrogen, halogen, trifluoromethyl, hydroxy, loweralkoxy or cyano;
m is 0, 1 or 2;
n is 3 or 4;
p is 2, 3 or 4;
with the following provisos;
when $R_1$ and $R_2$ are hydrogen and $R_5$ is 4-pyridyl, $R_3$ and $R_4$ taken together cannot be a carbonyl group; and
when $R_3$ and $R_4$ are hydrogen and $R_5$ is 4-pyridyl, $R_1$ and $R_2$ taken together cannot be a carbonyl group; and
when $R_1$ and $R_3$ are hydrogen and $R_5$ is 4-pyridyl, $R_2$ and $R_4$ cannot be OH; and
when $R_3$ and $R_4$ taken together form a carbonyl group, $R_2$ is OH and $R_5$ is 4-pyridyl, $R_1$ cannot be $C_6H_5$;
or a pharmaceutically acceptable addition salt thereof, or where applicable, a geometric or optical isomer or racemic mixture thereof.

This invention also relates to a process for making these compounds, and to pharmaceutical compositions, and a method of using the compounds as serotonin reuptake inhibitors.

The compounds of this invention are useful as serotonin reuptake inhibitors and as such may be useful for the treatment of depression, obsessive-compulsive disorders (OCD), stuttering and trichotillomania.

Unless otherwise stated or indicated, the following definitions shall apply throughout the specification and appended claims.

The term "lower" shall mean the group it is describing contains from 1 to 6 carbon atoms.

The term loweralkyl shall mean a straight or branched alkyl group having from 1 to 6 carbon atoms, e.g., methyl, ethyl, n-propyl, isopropyl, n-butyl, isobutyl, sec-butyl, t-butyl and straight and branched chain pentyl and hexyl.

The term halogen shall mean fluorine, chlorine, bromine or iodine.

The term aryl shall mean a phenyl group substituted with 0, 1 or 2 substituents each of which is independently loweralkyl, loweralkoxy, halogen, trifluoromethyl or nitro.

Throughout the specification and appended claims, a given chemical formula or name shall encompass all stereo and optical isomers where such isomers exist.

Additionally, a given chemical formula or name shall encompass the pharmaceutically acceptable addition salts thereof.

In a preferred embodiment of this invention are compounds of formula I wherein $R_1$ is hydrogen, loweralkyl, aryl, arylloweralkyl or —$(CH_2)_n NR_6R_7$;
where $R_6$ and $R_7$ are loweralkyl; and n is 3;
$R_2$ is hydrogen or $OR_9$; where $R_9$ is hydrogen; or
$R_1$ and $R_2$ taken together form

$R_3$ is hydrogen or;
$R_4$ is hydrogen or $OR_9$; where $R_9$ is hydrogen;
or $R_3$ and $R_4$ taken together form a carbonyl group;
$R_5$ is

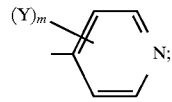

where Y is halogen and m is 1;
or $R_5$ is

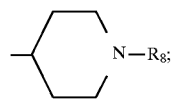

where $R_8$ is arylloweralkyl.

More preferred are compounds of formula I wherein $R_1$ is hydrogen, loweralkyl, phenyl, or $(CH_2)_n NR_6R_7$, where $R_6$ and $R_7$ are loweralkyl; n is 3;
$R_2$ is hydrogen or $OR_9$; where $R_9$ is hydrogen;
or $R_1$ and $R_2$ together form

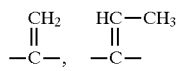

$R_3$ is hydrogen;
$R_4$ is hydrogen or $OR_9$; where $R_9$ is hydrogen; or
$R_3$ and $R_4$ taken together form a carbonyl group.

The compounds of this invention are prepared in the following manner. The substituents X, Y, $R_1$ to $R_{10}$, m and n are as defined above unless indicated otherwise.

PREPARATION

Synthetic Route A

To prepare compounds of formula I wherein $R_1$, $R_2$, $R_3$ and $R_4$ are hydrogen, 2,3-dihydro-1H-isoindole of the formula

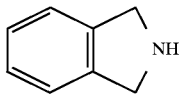

is reacted with a 4-chloro-substituted-pyridine hydrochloride to afford compound Ia of the formula

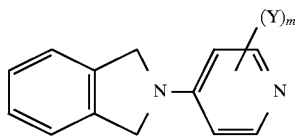

where $(Y)_m$ is determined by the substituent on the 4-chloropyridine hydrochloride. This reaction typically takes place in a polar, aprotic solvent such as N,N-dimethylformamide or N-methylpyrrolidinone at a temperature of about 90°–150° C. for 1 to 8 hours.

2,3-dihydro-1H-isoindole is known in the literature and can be prepared as described in Organic Syntheses, collective Vol. V., p. 406 and p. 1065.

Synthetic Route B

To prepare compounds of formula I wherein $R_1$, $R_2$, $R_3$ and $R_4$ are other than hydrogen, a compound of the formula

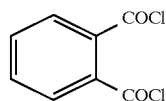

is reacted with a primary amine of the formula

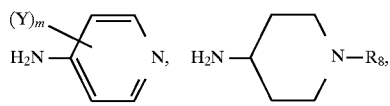

or $H_2N(CH_2)_7NR_6R_7$ to afford compounds of formula II

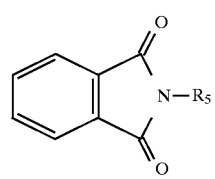

Compound II where $R_5$ is

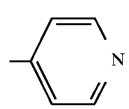

is N is known in the art and is described in J. Het. Chem., 16, 645 (1979).

Compound II can be reacted with a loweralkyl magnesium halide to afford compound III of the formula

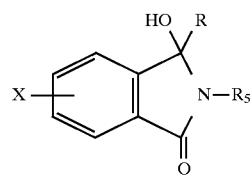

where R is loweralkyl. This reaction typically takes place in a suitable solvent such as tetrahydrofuran at a temperature of about 0° to 40° C. for 0.5 to 24 hours.

Compound III (R≠H) can be further reacted by treating it with phosphorus pentoxide or other dehydrating agents to prepare compound IV of the formula

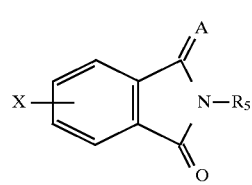

where A is

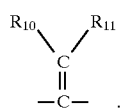

Stereoisomers of this compound may be prepared and separated by means known in the art.

Alternatively, compound III can be reduced with lithium aluminum hydride or other suitable reducing agents in the presence of a catalyst such as $AlCl_3$ to produce compounds of formula I where $R_1$, $R_2$, $R_3$ and $R_4$ are determined by the starting group on the precursor compound. For instance, if $R_3$ and $R_4$ together form a carbonyl group and $R_2$ is OH and $R_1$ is dimethylaminopropyl, the final reduced compound will have $R_1$ as dimethylaminopropyl. These reactions are typically conducted in a suitable solvent such as tetrahydrofuran at a temperature of about 0° to 40° C. for 0.5 to 24 hours. It is necessary to stir the reaction mixture for a period of 20 minutes to 2 hours before quenching with a saturated solution of $NH_4Cl$ or other suitable acid.

To prepare compounds of formula I where one of $R_1$, $R_2$, $R_3$ or $R_4$ is phenyl, compound III where R is phenyl is reduced as previously shown to afford compound V of the formula

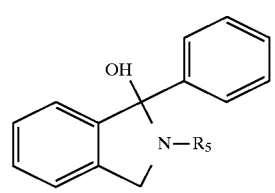

Compound V is subsequently treated with trifluoroacetic acid followed by a reducing agent such as triethylsilane to remove the OH group. This reaction is typically conducted in a suitable solvent such as dichloromethane, with stirring.

Compound IV can be further reduced by catalytic hydrogenation utilizing a noble material catalyst to afford compound VI of the formula

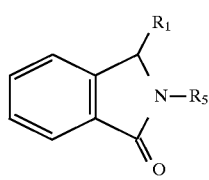

(VI)

where $R_1$ is loweralkyl, aryl or arylloweralkyl. Noble metal catalysts useful for this reaction include palladium, platinum or rhodium; with palladium the preferred choice. The noble metal catalyst can be in the form of the metal supported on an inert surface, such as carbon, or as an oxide or salt. This reaction typically takes place in a suitable solvent such as tetrahydrofuran or ethanol in a shaker vessel at about 25° to 50° C. for 5 to 10 hours.

Compound VI can be further reacted to reduce the carbonyl group to an OH group by treatment with lithium aluminum hydride. The OH group can be removed, as previously described, by treatment with trifluoroacetic acid and triethylsilane.

The compounds of the invention may be useful for the treatment of depression and/or OCD by virtue of their ability to inhibit the reuptake of serotonin. This is shown in the following assay.

[$^3$H]-Serotonin Uptake in Rat Whole Brain and Hypothalamic Synaptosomes

Some researchers have suggested that subjects with serotonergic hypofunction comprise a biochemical subgroup of depressed patients. Others claim that altered serotonergic function determines the change associated with obsessive-compulsive disorder.

This activity is determined in an assay which measures [$^3$H]-serotonin uptake in rat whole brain and hypothalamic synaptosomes. The assay described below is used as a biochemical screen for potential antidepressants which block serotonin (5-hydroxytryptamine (5HT)) uptake.

[$^3$H]-5HT transport has been characterized in the central nervous system tissue and found to be saturable, sodium and temperature-dependent, inhibited by ouabain, metabolic inhibitors, tryptamine analogs and tricyclic antidepressants.

Procedure

A. Animals

Male CR Wistar rats (100–125 g)

B. Reagents

1. Krebs-Henseleit Bicarbonate Buffer, pH 7.4 (KHBB): Prepare a 1 liter batch containing the following salts.

|  | grams/l | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |

Prior to use add to 200 ml, per assay:

|  |  |  |
|---|---|---|
| Dextrose | 2 mg/ml | 11.1 |
| Iproniazid phosphate | 0.30 mg/ml | 0.1 |

The batch is aerated for 60 minutes with 95% $O_2$/5% $CO_2$, the pH is checked to insure it is at 7.4±0.1, then add bovine serum albumin (Sigma cat# A-7906) 1 mg/ml.

2. Filtration buffer:

Make a 4 liter batch, containing the following salts:

|  | grams/4L | mM |
|---|---|---|
| NaCl | 31.68 | 135.5 |
| KCl | 1.40 | 4.7 |
| MgSO$_4$.7H$_2$O | 1.16 | 1.2 |
| HEPES | 9.54 | 10.0 |
| CaCl$_2$ | 0.56 | 1.3 |
| BSA | 4.0 | 1 mg/ml |

Maintain on ice.

3. Sucrose solution: 0.32M sucrose containing 5 mM HEPES and 0.1 mM EDTA; pH to 7.3 using Tris base.

4. A 0.1 mM stock solution of serotonin creatinine $SO_4$ is made up in 0.01N HCl. This is used to dilute the specific activity of the radiolabeled 5HT.

5. 5-[1,2-$^3$H(N)]-Hydroxytiyptamine creatinine sulfate (serotonin), specific activity 20-30 Ci/mmol, is used.

The final desired concentration of [$^3$H]-5HT in the assay is 50 nM. The dilution factor is 0.8. The KHBB is made up to contain 62.5 nM of [$^3$H]-5HT.

Add to 100 ml of KHBB.

| A) 56.1 µl of 0.1 mM 5HT = | 56.1 nM |
|---|---|
| B) 0.64 nmol of [$^3$H]-5HT = | 6.4 nM |
|  | 62.5 nM |

6. For most assays, a 0.5 mM stock solution of the test compound is made up initially in either 10 µl of glacial acetic acid, 100 µl DMSO or 10 µl of the recrystallization solvent, to which is added approximately 10 ml of distilled water. Compounds are initially screened in duplicate at 3 concentrations ($10^{-8}$, $10^{-7}$ and $10^{-6}$M) made up in water. For those compounds demonstrating activity at $\leq 10^{-7}$ in the initial screen, $EC_{50}$s are determined from 7 concentrations: $10^{-9}$ through $10^{-6}$. Higher or lower concentration ranges may be used depending on the potency of the compound. To ensure consistency, the standard chlomipramine is run with each assay.

C. Tissue Preparation

The Percoll method for preparing synaptosomes has been modified from Nagy, A., Delgado-Escueta, A. V. J. Neurochem. 43, 1114 (1984) and Dunkley, P. R., Jarvie, R. E., Heath, J. W., Kidd, G. J., Rostas, J. A. P. Brain Research 372, 115 (1986). Male Wistar rats are decapitated and the brain rapidly removed. Whole brain (minus cerebellum) is weighed and homogenized in 15 volumes of ice cold Sucrose solution using a Potter-Elvejhem homogenizer. The following procedures are performed on ice. Homogenization should be done with 4–5 up and down strokes at medium speeds (setting 4.5 to 5) to minimize synaptosome lysis. The homogenate is centrifuged at 1000 g (3000 rpm, Sorvall SS-34 rotor) for 10 minutes at 0°–4° C. The supernatant is removed and approximately 10 ml per tube is carefully layered onto a discontinuous Percoll (Sigma cat# P-1644) gradient: 21% Percoll in Sucrose solution at the bottom (15 ml per tube) and 10% Percoll in the middle (10 ml; colored with a few drops of phenol red for visibility).

The Percoll gradient tubes are carefully placed into a Beckman SW-28 swinging bucket rotor and spun in a Beckman XL90 ultracentrifuge using the following program: speed, 11,000 rpm (15,000 g) for 30 minutes at 4° C.; slow acceleration and deceleration (acceleration setting 9; deceleration setting 3). Tubes are carefully removed, and the top layer and the top part of the middle (red) layer are discarded using a pasteur pipette. The synaptosomes are located in the white fluffy band at the interface between the 10% and 21% Percoll layers. This is carefully removed, placed in a centrifuge tube, diluted with KHBB and spun at 21,000 g (13,000 rpm, Sorvall SS-34 rotor). The pellet (synaptosomes) is resuspended in KHBB (10 vol per gram original brain wet weight; 1 brain minus cerebellum weighs approximately 1.2 g; 2.5 brains are needed per typical assay).

D. Assay

| | |
|---|---|
| 800 µl | KHBB with [$^3$H]-5HT |
| 20 µl | Vehicle or appropriate drug |
| 200 µl | Tissue suspension concentration |

200 µl of the tissue suspension are added to each of 24 tubes (at a time) containing the 20 µl of vehicle or drug on ice. Three minutes later, 800 µl of KHBB containing [$^3$H]-5HT are added, and the tubes are vortexed. The rack containing the 24 tubes is moved from the ice bath to a water bath set at 37° C. The tubes are incubated for 5 minutes under 95% $O_2$/5% $CO_2$. Uptake is terminated by filtration through GF/B filter strips using a Brandel cell harvester (filter strips are presoaked in ice cold filtration buffer). Tubes are washed once with 5 ml of ice cold filtration buffer. Filter disks are placed in scintillation vials to which are added 10 ml of scintillation fluid (EcoScint). Filters are allowed to sit overnight before being counted.

For each assay, 3 tubes each are incubated with 20 µl of vehicle at both 37° C. and 0° C. Active uptake is the difference between cpm taken up at 37° C. and 0° C. Percent inhibition at each concentration is the mean of two deteminants. $IC_{50}$ values are derived from log probit analysis using #46 Litchfield and Wilcoxon I: confidence limits of $IC_{50}$ Pharnacologic Calculation System - version 4.0.

| Compound | 5-HT Uptake $IC_{50}$ (µM) |
|---|---|
| 2,3-Dihydro-2-(4-pyridyl)-1H-isoindole maleate | 0.88 |
| 2,3-Dihydro-1-methyl-2-(4-pyridyl)-1H-isoindole fumarate | 0.736 |
| 2,3-dihydro-1-propyl-2-(4-pyridyl)-1H-isoindole maleate | 0.725 |
| 2,3-dihydro-1-ethyl-2-(4-pyridyl)-1H-isoindole maleate | 1.14 |
| 2,3-dihydro-1-(2-methylpropyl)-2-(4-pyridyl)-1H-isoindol maleate | 0.849 |
| Standard Drugs | |
| Amitriptyline | 0.091 |
| Fluoxetine | 0.042 |

Relief from depression and/or OCD is achieved when the compounds of the present invention or compounds which form in vivo compounds of the present invention, e.g. bioprecursors, are administered or provided to a subject requiring such treatment as an effective oral, parenteral, or intravenous dose of from 1 to 100 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Effective quantities of the compounds of the present invention or compounds which form in vivo compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered or provided in the form of their pharmaceutically acceptable addition salts for purposes of stability, convenience of crystallization, increased solubility and the like.

Preferred pharinaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention or the compounds which form in vivo the compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain or form at least 0.5% of active compound, but may be varied depending upon the particular form and may conveniently be between 4% to about 75% of the weight of the unit. The amount of compound present in such composition is such that a suitable dosage of active compound will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium stearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the doseage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention or the compounds which form in vivo the compounds of the present invention may be incorporated into a solution or suspension. These preparations should contain at least 0.1% of the aforesaid compound, but may be varied between 0.5 and about 30% of the weight thereof. The amount of compound in such compositions is such that a suitable dosage of active compound will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of pharmaceutical composition formulations such as tablets, suppository and emulsions are given below:

PHARMACEUTICAL FORMULATIONS
TABLET:

| Ingredients | In each tablet |
| --- | --- |
| Active ingredient | 300 mg |
| Polyvinylpyrrolidone | 22.5 mg |
| Lactose | 61.75 mg |
| Alcohol 3A - 200 proof | 4.5 mg |
| Stearic acid | 9 mg |
| Talc | 13.5 mg |
| Corn starch | 43.25 mg |

Blend the active compound, polyvinylpyrrolidone and lactose together and pass through a 40-mesh screen. Add the alcohol slowly and knead well. Screen the wet mass through a 4-mesh screen. Dry granulation at 50° C. overnight. Screen the dried granulation through a 20-mesh screen. Bolt the stearic acid, talc and corn starch through 60-mesh screen prior to mixing by tumbling with the granulation. Compress using 7/16 -in. standard concave punch. 10 tablets should weigh 4.5 g.

SUPPOSITORY:

| Ingredients | In each suppository |
| --- | --- |
| Active ingredient | 300 mg |
| Glycerin | 3000 mg |
| Purified water | 200 mg |

The glycerin is heated in a suitable container to about 120° C. The drug is dissolved, with gentle stirring, in the heated glycerin after which the purified water is added, mixed and the hot mixture immediately poured into a suitable mold.

EMULSION:

| Ingredients | Amount |
| --- | --- |
| Gelatin Type A* | 4 g |
| Active Ingredient | 360 mg |
| Flavor as desired | |
| Alcohol | 30 ml |
| Oil | 250 ml |
| Purified water, to make | 500 ml |

*prepared from acid-treated precursors; used at a pH of ca. 3.2.

Add the gelatin and the drug to about 300 ml of purified water, allow to stand for a few minutes, heat until the gelatin is dissolved, then raise the temperature to about 98° C., and maintain this temperature for about 20 min. Cool to 50° C., add the flavor, the alcohol, and sufficient purified water to make 500 ml. Add the oil, agitate the mixture thoroughly, and pass it through a homogenizer or a colloid mill until the oil is completely and uniformly dispersed.

Examples of compounds of the invention include:
2,3-dihydro-2-(4-pyridyl)-1H-isoindole maleate;
2,3-dihydro-2-(3-fluoro-4-pyridyl)- 1 H-isoindole maleate;
2,3-dihydro-3-hydroxy-3-methyl-2-(4-pyridyl)-1H-isoindol-1-one fumarate;
2,3-dihydro-1-methyl-2-(4-pyridyl)-1H-isoindole fumarate;
2,3-dihydro-3-hydroxy-3-ethyl-2-(4-pyridyl)-1H-isoindol-1-one maleate;
2,3-dihydro-3-methylene-2-(4-pyridyl)-1H-isoindol-1-one;
2,3-dihydro-3-methyl-2-(4-pyridyl)-1H-isoindol-1-one maleate;
2,3-dihydro-(E)-3-ethylene-2-(4-pyridyl)-1H-isoindol-1-one maleate;
2,3-dihydro-(Z)-3-ethylene-2-(4-pyridyl)-1H-isoindol-1-one maleate;
2,3-dihydro-3-ethyl-2-(4-pyridyl)-1H-isoindol-1-one maleate;
2,3-dihydro-1-ethyl-2-(4-pyridyl)-1H-isoindole maleate;
2,3-dihydro-1- propyl-2-(4-pyridyl)-1H-isoindole maleate;
2,3-dihydro-1-(2-methylpropyl)-2-(4-pyridyl)-1H-isoindole maleate;
2,3-dihydro-1-(dimethylaminopropyl)-2-(4-pyridyl)-1H-isoindole maleate;
2,3-dihydro-1-hydroxy-1-phenyl-2-(4-pyridyl)-1H-isoindole;
2-(1-benzyl-4-piperidinyl)-2,3-dihydro-1-ethyl-1H-isoindole dimaleate; and
2,3-dihydro-1-phenyl-2-(4-pyridyl)-1H-isoindole maleate.

The following examples are for illustrative purposes and are not to be construed as limiting the invention disclosed herein. All temperatures are given in degrees centigrade (°C.) unless indicated otherwise.

EXAMPLE 1

2,3-Dihydro-2-(4-Pyridyl)-1H-Isoindole Maleate

A mixture of 2,3-dihydro-1H-isoindole (5.87 g) and 4-chloropyridine hydrochloride (8.13 g) in 30 ml N-methylpyrrolidinone was heated at 130° C. for 2 hours. The reaction was quenched into water and washed three times with ethyl acetate. The aqueous solution was basified with $Na_2CO_3$ and a solid was filtered, rinsed with water and dried. The solid was passed through a column of florisil (5% methanol/ethyl acetate) to give 2.78 g of a solid. A 1.60 g portion of this solid was dissolved in methanol, treated with 1.1 equivalents of maleic acid and the salt was crystallized out by the addition of ether to give 1.48 g of a solid, mp: 223°–224° C. The solid was recrystallized from methanol to give 1.10 g of crystals, mp: 229°–230° C. (dec).

Analysis: Calculated for $C_{13}H_{12}N_2 \bullet C_4H_4O_4$: 65.38%C; 5.16%H; 8.97%N; Found: 65.30%C.; 5.07%H; 8.91%N.

EXAMPLE 2

2,3-Dihydro-2-(3-Fluoro-4-Pyridyl)-1H-Isoindole Maleate

A mixture of 2,3-dihydro-1H-isoindole (5.27 g) and 4-chloro-3-fluoropyridine hydrochloride (8.17 g) in 20 ml N,N-dimethylformamide was heated at 100° C. for 6 hours. The reaction was quenched into water, basified with solid $Na_2CO_3$ and extracted three times with ethyl acetate. The organics were washed twice with water, dried (MgSO$_4$) and the solvent was concentrated to give an oil which was purified via flash chromatography (ethyl acetate/DCM) to give 1.20 g of a solid, mp: 124°–133° C. This solid was dissolved in methanol, treated with 1.1 equivalents of maleic acid and the salt was crystallized out by the addition of ether to give 1.20 g of a powder, mp: 204°–208° C.

Analysis: Calculated for C$_{13}$H$_{11}$FN$_2$●C$_4$H$_4$O$_4$: 61.82%C; 4.58%H; 8.48%N; Found: 61.86%C.; 4.39%H; 8.43%N.

EXAMPLE 3

2,3-Dihydro-3-Hydroxy-3-Methyl-2-(4-Pyridyl)-1H-Isoindol-1-One Fumarate

A solution of 2-(4-pyridyl)phthalimide (8.08 g) in 250 ml tetrahydrofuran was treated with 14.4 ml of a 3.0 Molar solution of methyl magnesium bromide. After stirring for 1 hour, the reaction was quenched with saturated NH$_4$Cl solution, diluted with ethyl acetate/water and the organics were washed once with water and dried (saturated NaCl, MgSO$_4$). The solvent was removed to give 7.20 g of a powder. A 2.1 g portion was recrystallized from ethyl acetate, and the resulting solid was dissolved in methanol, treated with 1.1 equivalents of fumaric acid and the salt was crystallized out of solution by the addition of ether to give 1.83 g of a solid, mp: 213°–214° C. The solid was then recrystallized from ethyl acetate/heptane to give 1.52 g of a powder, mp: 213.5°–214° C. (dec).

Analysis: Calculated for C$_{14}$H$_{12}$N$_2$O$_2$●C$_4$H$_4$O$_4$: 60.67%C.; 4.53%H; 7.86%N; Found: 60.74%C.; 4.35%H; 7.78%N.

EXAMPLE 4

2,3-Dihydro-1-Methyl-2-(4-Pyridyl)-1H-Isoindole Fumarate

A solution of 2,3-dihydro-1-hydroxy-3-methyl-2-(4-pyridyl)-1H-isoindole (1.19 g) in 20 ml dichloromethane was treated with 8 ml trifluoroacetic acid followed by treatment with triethylsilane (1.16 ml). After stirring for 10 minutes, the reaction was added to dilute K$_2$CO$_3$ solution and the aqueous was extracted three times with ethyl acetate. The combined organics were washed with water, dried and concentrated to give 0.66 g of an oil. The oil was dissolved in methanol and treated with 1.1 equivalents of fumaric acid and the salt was crystallized out by the addition of ether to give 0.60 g of a solid. The solid was combined with another lot and recrystallized from ethanol/ethyl acetate to give 0.62 g of a powder, mp: 185°–186° C. (dec).

Analysis: Calculated for C$_{14}$H$_{14}$N$_2$●C$_4$H$_4$O$_4$: 66.25%C.; 5.56%H; 8.58%N; Found: 65.99%C.; 5.49%H; 8.42%N.

EXAMPLE 5

2,3-Dihydro-3-Hydroxy-3-Ethyl-2-(4-Pyridyl)-1H-Isoindol-1-One Maleate

A solution of 2-(4-pyridyl)phthalimide (6.02 g) in 200 ml tetrahydrofuran was treated with a total of 11.8 ml of a 3.0 Molar solution of ethyl magnesium bromide. After stirring for 1 hour, the reaction was quenched with saturated NH$_4$Cl solution, diluted with ethyl acetate/water and the organics were washed twice with saturated NaCl solution and dried (MgSO$_4$). The solvent was removed to give 6.26 g of a powder, mp: 197°–201° C. A 2.23 g portion was recrystallized from ethyl acetate/heptane and the resulting solid was dissolved in methanol, treated with 1.1 equivalents of maleic acid and the solvent was removed to give a solid which was recrystallized from methanol/ether giving 1.31 g of a powder, mp: 130°–136° C. (dec).

Analysis: Calculated for C$_{15}$H$_{14}$N$_2$O$_2$●C$_4$H$_4$O$_4$: 61.62%C.; 4.90%H; 7.56%N; Found: 61.95%C.; 4.50%H; 7.56%N.

EXAMPLE 6

2,3Dihydro-3-Methylene-2-(4-Pyridyl)-1H-Isoindol-1-One

A mixture of 2,3-dihydro-3-hydroxy-3-methyl-2-(4-pyridyl)-1H-isoindol-1-one (10.20 g) and phosphorus pentoxide (6.03 g) was heated under vacuum at 200° C. for 20 minutes. Ice water was then added and the mixture was basified with K$_2$CO$_3$ solution. The resulting solid was filtered, dried and passed through a column of florisil (ethyl acetate) to give 6.23 g of a solid. A 2.0 g portion was recrystallized from methanol to give 1.37 g of platelets, mp: 173°–174° C.

Analysis: Calculated for C$_{14}$H$_{10}$N$_2$O: 75.66%C.; 4.54%H; 12.60%N; Found: 75.48%C.; 4.46%H; 12.72%N.

EXAMPLE 7

2,3-Dihydro-3-Methyl-2-(4-Pyridyl)-1H-Isoindol-1-One Maleate

A solution of 2,3-dihydro-3-methylene-2-(4-pyridyl)-1H-isoindol-1-one (4.22 g) in 200 ml tetrahydrofuran was added to a suspension of 10% palladium on carbon (0.95 g) in 50 ml THF. The reaction vessel was pressurized to 45 psi with hydrogen and shaken for 6 hours. Filtration of the catalyst and concentration of the solvent gave 3.85 g of a solid. A 1.37 g portion was dissolved in methanol, treated with 1.1 equivalents of maleic acid and the salt was crystallized out by the addition of ether to give 1.69 g of platelets, mp: 149°–151° C. (dec).

Analysis: Calculated for C$_{14}$H$_{12}$N$_2$O●C$_4$H$_4$O$_4$: 63.53%C; 4.74%H; 8.23%N; Found: 63.52%C.; 4.63%H; 8.14%N.

EXAMPLE 8a 2,3-Dihydro-(E)-3-Ethylene-2-(4-Pyridyl)-1H-Isoindol-1-One Maleate A mixture of 2,3-dihydro-3-hydroxy-3-ethyl-2-(4-pyridyl)-1H-isoindol-1-one (7.37 g) and phosphorus pentoxide (4.11 g) was heated under vacuum at 205° C. for 1.5 minutes. Ice water was then added and the mixture was basified with K$_2$CO$_3$ solution. The resulting solid was filtered, dried and passed through a column of florisil (ethyl acetate) to give 4.91 g of a solid which was a mixture of stereoisomers. A portion of each isomer was obtained pure by purification of the mixture via HPLC (25–50% ethyl acetate/DCM).

A 1.40 g portion of the E-isomer was dissolved in methanol, treated with 1.1 equivalents of maleic acid and the solvent was concentrated to a solid. The solid was recrystallized from methanol to give 1.25 g of crystals, mp: 147°–149° C. (dec).

Analysis: Calculated for C$_{15}$H$_{12}$N$_2$O●C$_4$H$_4$O$_4$: 64.77%C.; 4.58%H; 7.95%N; Found: 64.62%C.; 4.39%H; 7.94%N.

EXAMPLE 8b 2,3-Dihydro-(Z)-3-Ethylene-2-(4-Pyridyl)-1H-Isoindol-1-One Maleate A 1.42 g portion of the Z-isomer from the mixture of stereoisomers prepared in Example 8a was dissolved in methanol, treated with 1.1 equivalents of maleic acid and the solvent was concentrated to a solid. The solid was recrystallized from methanol to give 1.55 g of a powder, mp: 148°–150° C. (dec).

Analysis: Calculated for $C_{15}H_{12}N_2O \bullet C_4H_4O_4$: 64.77%C.; 4.58%H; 7.95%N; Found: 64.72%C.; 4.28%H; 7.96%N.

EXAMPLE 9

2,3-Dihydro-3-Ethyl-2-(4-Pyridyl)-1H-Isoindol-1-One Maleate

A solution of 2,3-dihydro-3-ethylene-2-(4-pyridyl)-1H-isoindol-1-one (2.90 g) in 100 ml tetrahydrofuran was added to a suspension of 10% palladium on carbon (0.95 g) in 50 ml THF. The reaction vessel was pressurized to 50 psi with hydrogen and shaken for 7 hours. Filtration of the catalyst and concentration of the solvent gave 2.65 g of a solid, mp: 126°–130° C. A 1.36 g portion was dissolved in methanol, treated with 1.1 equivalents of maleic acid and the salt was crystallized out by the addition of ether to give 1.76 g of a solid, mp: 152°–153° C. (dec).

Analysis: Calculated for $C_{15}H_{14}N_2O \bullet C_4H_4O_4$: 64.40%C.; 5.12%H; 7.91%N; Found: 64.56%C.; 5.21%H; 7.90%N.

EXAMPLE 10

2,3-Dihydro-1-Ethyl-2-(4-Pyridyl)-1H-Isoindole Maleate

A solution of 2,3-dihydro-3-ethyl-2-(4-pyridyl)-1H-isoindol-1-one (6.15 g) in 150 ml tetrahydrofuran was treated with 31 ml of a 1 Molar solution of lithium aluminum hydride. The solution was stirred for 0.5 hours and then quenched with a saturated solution of $NH_4Cl$ in water. The mixture was diluted with ethyl acetate and the inorganics were filtered; the organic phase was dried ($MgSO_4$) and the solvent was removed leaving 5.60 g of a solid.

A solution of 2,3-dihydro-1-hydroxy-3-ethyl-2-(4-pyridyl)-1H-isoindole (3.87 g) in 60 ml dichloromethane was treated with 24 ml of trifluoroacetic acid followed by treatment with triethylsilane (3.50 ml). After stirring for 20 minutes, the reaction was added to dilute $K_2CO_3$ solution and the aqueous was extracted three times with ethyl acetate. The combined organics were washed with water, dried and concentrated to give 3.02 g of an oil. A 1.38 g portion was dissolved in methanol and treated with 1.1 equivalents of maleic acid and the salt was crystallized out by the addition of ether to give 1.55 g of crystals, mp: 138°–139° C. (dec).

Analysis: Calculated for $C_{15}H_{16}N_2 \bullet C_4H_4O_4$: 67.05%C.; 5.92%H; 8.23%N; Found: 66.84%C.; 5.95%H; 8.18%N.

EXAMPLE 11

2,3-Dihydro-1-Propyl-2-(4-Pyridyl)-1H-Isoindole Maleate

A solution of 3-hydroxy-3-propyl-2-(4-pyridyl)-isoindol-1-(2H)-one (7.0 g) in 150 ml tetrahydrofuran was added to a mixture of lithium aluminum hydride (52.2 ml of a 1 molar solution diluted with 50 ml THF) treated with 2.32 g of aluminum chloride. The reaction was stirred for 0.5 hours and then quenched with a saturated $NH_4Cl$ solution. The mixture was diluted with ethyl acetate; the salts were filtered and the organics were dried ($MgSO_4$).

The desired compound was purified via flash chromatography (3% triethylamine/ethyl acetate) to give 2.94 g of an oil. A 1.26 g portion was dissolved in methanol, treated with 1.1 equivalents of maleic acid and the salt was allowed to crystallized out to give 1.35 g of a powder, mp: 142°–144° C. (dec).

Analysis: Calculated for $C_{16}H_{18}N_2 \bullet C_4H_4O_4$: 67.78%C.; 6.26%H; 7.90%N; Found: 67.63%C.; 6.08%H; 7.76%N.

Following a procedure similar to that described in Example 11, the following compounds were prepared:

$$X-\underset{H}{\overset{R_2}{\underset{|}{\diagdown}}}\overset{R_1}{\underset{H}{\diagup}}N-R_5$$

| EX | $R_1$ | $R_2$ | $R_5$ | m.p. (°C.) | Salt |
|----|-------|-------|-------|------------|------|
| 11a | 2-methylpropyl | — | 4-pyridyl | 139–141 (dec) | maleate |
| 11b | 3-dimethyl-aminopropyl | — | 4-pyridyl | 221–222 (dec) | sesqui-fumarate |
| 11c | phenyl | OH | 4-pyridyl | 172–174 (dec) | — |
| 11d | ethyl | — | 1-benzyl-4-piperidinyl | 180–182 (dec) | dimaleate |

EXAMPLE 12

2,3-Dihydro-1-Phenyl-2-(4-Pyridinyl)-1-Isoindole Maleate

A solution of 2,3-dihydro-1-hydroxy-3-phenyl-2-(4-pyridinyl)-1H-isoindole (2.80 g) in 60 ml dichloromethane was treated with 15 ml trifluoroacetic acid followed by treatment with triethylsilane (2.20 ml). After stirring for 20 minutes, the reaction was added to dilute $K_2CO_3$ solution and the aqueous was extracted twice with ethyl acetate. The combined organics were washed with water, dried and concentrated to give a semi-solid which was triturated with ether to give 1.70 g of a powder, mp: 187°–191° C. The powder was dissolved in methanol, treated with 1.1 equivalents of maleic acid and the salt was crystallized out by the addition of ether to give 1.80 g of a powder, mp: 164°–166° C. (dec).

Analysis: Calculated for $C_{19}H_{16}N_2 \bullet C_4H_4O_4$: 71.12%C.; 5.19%H; 7.21%N; Found: 71.01%C.; 5.24%H; 7.25%N.

We claim:

1. A compound of the formula $$X-\underset{R_4\ R_3}{\overset{R_2\ R_1}{\diagup\diagdown}}N-R_5$$

wherein $R_1$ is hydrogen, loweralkyl, aryl, arylloweralkyl, or —$(CH_2)_n NR_6 R_7$; $R_2$ is hydrogen or $OR_9$; $R_1$ and $R_2$ taken together with the carbon atom to which they are bound form a group of the formula

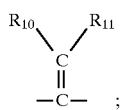

$R_3$ is hydrogen;
$R_4$ is hydrogen or $OR_9$;
$R_5$ is a group of the formula

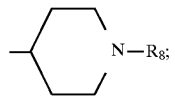

$R_6$ is loweralkyl or arylloweralkyl;
$R_7$ is loweralkyl or arylloweralkyl;
$R_8$ is hydrogen, loweralkyl or arylloweralkyl;
$R_9$ is hydrogen or loweralkyl;

$R_{10}$ is hydrogen or loweralkyl;
$R_{11}$ is hydrogen or loweralkyl;
X is hydrogen, halogen, trifluoromethyl, hydroxy, loweralkoxy or cyano;
n is 3 or 4;
a pharmaceutically acceptable addition salt thereof or, where applicable, a geometric isomer, or optical isomer, or racemate thereof.

2. A compound as claimed in claim 1 wherein $R_1$, $R_2$, $R_3$, and $R_4$ are hydrogen or loweralkyl, and $R_8$ is arylloweralkyl; or a pharmaceutically acceptable addition salt thereof or, where applicable, a geometric isomer, or optical isomer, or racemate thereof.

3. The compound as claimed in claim 2 which is 2-(1-benzyl-4-piperidinyl)-2,3-dihydro-1-ethyl-1H-isoindole.

* * * * *